(12) United States Patent
Tucker et al.

(10) Patent No.: US 8,738,143 B2
(45) Date of Patent: May 27, 2014

(54) MEDICAL DEVICE FOR ISOMETRIC STIMULATION TO IMPROVE BLOOD FLOW

(75) Inventors: Arthur Tudor Tucker, London (GB); Duncan Shirreffs Bain, Stanmore (GB)

(73) Assignee: Sky Medical Technology Ltd., Buckinghamshire (GB)

( * ) Notice: Subject to any disclaimer, the term of this patent is extended or adjusted under 35 U.S.C. 154(b) by 1654 days.

(21) Appl. No.: 11/791,296

(22) PCT Filed: Nov. 21, 2005

(86) PCT No.: PCT/GB2005/050205
§ 371 (c)(1),
(2), (4) Date: Mar. 20, 2008

(87) PCT Pub. No.: WO2006/054118
PCT Pub. Date: May 26, 2006

(65) Prior Publication Data
US 2012/0041513 A1    Feb. 16, 2012

(30) Foreign Application Priority Data
Nov. 22, 2004 (GB) .................................. 0425632.7

(51) Int. Cl.
*A61N 1/36*    (2006.01)
*A61N 1/04*    (2006.01)

(52) U.S. Cl.
CPC ......... *A61N 1/36003* (2013.01); *A61N 1/36014* (2013.01); *A61N 1/0456* (2013.01)
USPC ............................................. 607/48; 607/144

(58) Field of Classification Search
CPC . A61N 1/0404; A61N 1/0452; A61N 1/0456; A61N 1/36; A61N 1/36003; A61N 1/36014
USPC ........................... 607/2, 3, 48, 115, 116, 144
See application file for complete search history.

(56) References Cited

U.S. PATENT DOCUMENTS

| | | | | | |
|---|---|---|---|---|---|
| 3,083,712 | A | * | 4/1963 | Keegan, Jr. ..................... | 607/48 |
| 4,976,264 | A | * | 12/1990 | Petrofsky ........................ | 607/48 |
| 5,358,513 | A | * | 10/1994 | Powell et al. .................. | 607/48 |

(Continued)

FOREIGN PATENT DOCUMENTS

| | | |
|---|---|---|
| JP | 2002-224227 | 8/2002 |
| JP | 2003-079749 | 3/2003 |
| WO | WO 99/64105 A1 | 12/1999 |
| WO | WO 02/056960 A2 | 7/2002 |

OTHER PUBLICATIONS

Tucker, "Augmentation of venous, arterial and microvascular blood supply in the leg by isometric neuromuscular stimulation via the peroneal nerve". Int J Angiol. 2010 Spring; 19(1): e31-e37.*

(Continued)

*Primary Examiner* — Carl H Layno
*Assistant Examiner* — Eugene Wu
(74) *Attorney, Agent, or Firm* — Wolf, Greenfield & Sacks, P.C.

(57) ABSTRACT

The present invention provides a method and device for reduction of or treatment of deep vein thrombosis (DVT), the method comprising causing isometric stimulation of the leg muscles to promote blood flow. Other embodiments provide treatment for other circulatory disorders of the lower limbs and/or the systemic circulation.

33 Claims, 9 Drawing Sheets

(56) References Cited

U.S. PATENT DOCUMENTS

| | | | |
|---|---|---|---|
| 5,643,331 A * | 7/1997 | Katz | 607/48 |
| 5,674,262 A * | 10/1997 | Tumey | 607/48 |
| 6,615,080 B1 | 9/2003 | Unsworth et al. | |
| 2002/0165590 A1 | 11/2002 | Crowe et al. | |
| 2003/0199943 A1* | 10/2003 | Katz et al. | 607/48 |
| 2004/0054384 A1* | 3/2004 | Nachum | 607/50 |
| 2004/0172097 A1 | 9/2004 | Brodard et al. | |
| 2005/0010265 A1* | 1/2005 | Baru Fassio et al. | 607/48 |

OTHER PUBLICATIONS

Geko devices: Studies and trials. <http://www.gekodevices.com/en-uk/studies/neuromuscular-electrostimulation-dvt-prophylaxis-nmes-studies-and-trials/>. Accessed Jan. 2, 2014.*

* cited by examiner

MEDICAL DEVICE FOR ISOMETRIC STIMULATION TO IMPROVE BLOOD FLOW

FIELD OF THE INVENTION

The present invention relates to a method and apparatus for reducing the incidence of deep vein thrombosis (DVT) and/or superficial vein thrombosis (SVT). Aspects of the invention relate to methods of operating such a device, and to methods and apparatus for preventing, reducing or alleviating other pathologies and symptoms associated with dysfunction of lower limb blood flow. Other pathologies and disorders may also be treated.

BACKGROUND TO THE INVENTION

Deep vein thrombosis (DVT) and superficial vein thrombosis (SWT) associated primarily but not exclusively with medium and long duration aviation travel, is becoming an increasing concern both to passengers and to airlines. For clarity and to prevent repetition, DWT described in this document refers to a pathological thrombotic event in the lower limb and may be taken to include the various presentations within the deep, superficial and communicating venous vessels of the lower limb.

DVT is a thrombosis that forms in the deep vein system of the lower leg, usually between the ankle and the upper calf. It is a common condition in patients receiving medical or surgical treatment in hospital. The condition is serious, potentially fatal, and very difficult to diagnose by external examination. The clot formation may develop very rapidly, detach from the wall of the vein and move through the blood stream before a problem is recognised. The clot may travel through the veins and lodge in essential organs such as the heart, brain or lungs, resulting in life-threatening conditions such as stroke, pulmonary embolism and myocardial infarction. The annual incidence of DVT in USA and Europe is approximately 160 per 100,000 and the rate of fatal PE is 50 per 100,000. Various studies have shown that about one third of patients undergoing major surgery without sufficient prophylaxis will develop DVT. In addition perioperative death due to pulmonary embolism has been shown to occur in 0.5% to 3.4% of patients undergoing major surgery.

The formation of a clot within the vein lumen is the result of interplay of various factors. The underlying pathophysiology suggests that three main factors are responsible for the development of thrombosis in the peripheral veins. This is termed as "Virchow's triad": i) damage to the vein wall (endothelium); ii) stasis of venous blood (slowing of blood flow); iii) a change in the constitution of the blood (i.e. increased coagulability). Since Virchow, other factors have been identified, but this theory is still accepted. Thrombi usually form in areas of slow or disturbed flow in large venous sinuses and in the valve pockets. The majority of thrombi originate in the soleal veins and valve pockets following surgery. Thrombi also form in vein segments, which have been subjected to direct trauma. A principal feature of clot formation relating to DVT is the pooling of stationary blood in the lower leg, as a result of staying immobile for too long, commonly with the leg in a dependant position. However, DVT may occur in lower limbs while lying supine, frequently where there are additional risk factors such as injury, inflammation or post surgery.

To understand the physiological processes responsible for DVT, it is first essential to describe the normal venous blood return of the lower limb.

During recumbency, (when a subject is lying down with the legs and the heart at the same level), blood flows evenly along the superficial and deep veins towards the heart, propelled by a relatively small force coming through the capillaries. This is known a 'vis-a-tergo' (force from behind) and is the residual force generated by the heart and transmitted through the microvascular bed to the veins.

However, during standing the highly efficient calf pump is the main mechanism of venous return. During motionless standing the veins are full with a pressure equal to the hydrostatic pressure of a column of blood extending from the point of measurement up to the level of the heart. The hydrostatic pressure at the ankle is approximately 90 mmHg. Venous return is aided by the 'vis-a-tergo' of the capillary bed, also by respiratory movements, particularly inspiration. The close proximity of arteries to veins also aids venous return, as pulsations of adjacent arteries may assist flow in veins with competent valves. Although these mechanisms aid venous return, long standing high venous pressures can result in oedema formation even in normal limbs.

The musculovenous pumps of the lower limb and the presence of competent venous valves play an important role in aiding venous return and decreasing venous pressure in the lower limb. There are three pumps: the foot pump, calf pump and thigh pump.

The venous foot pump assists in venous return from the lower limbs as follows. Weight bearing causes flattening of the plantar arch and stretching and narrowing of the plantar veins expelling blood upwards from the foot towards the calf segment.

The calf pump is the most efficient and the most powerful of the three pumps, and during exercise it becomes the principal mechanism of venous return. During rhythmic exercise such as walking, it decreases the volume of blood in the capacity vessels of the lower limb and thus more blood is available for redistribution to other regions such as the pulmonary vascular bed. During muscle contraction, blood is ejected from the calf veins and into the thigh where it is picked up by the thigh muscle pump. Competent valves prevent reflux of blood back into distal veins.

As a result of muscle pump contraction during walking, the venous pressure at the ankle (measured from the Long Saphenous Vein) is reduced from 90 mmHg down to approximately 25 mmHg in the normal limb. The effectiveness of the venous muscle pump is judged by its ability to decrease venous pressure, and in normal limbs venous pressure is reduced well below hydrostatic levels. By lowering the venous pressure, the calf pump reduces oedema formation, which would occur as a result of high pressures in the upright position. The muscle pump action together with competent valves thus reduces venous pressure and prevents oedema formation. The fall in venous pressure during exercise, results in an increase in the arteriovenous pressure gradient by nearly 50%. The calf muscle pump has been termed the 'peripheral heart'. The increased arteriovenous pressure gradient results in increased perfusion pressure in the distal tissues and increased perfusion. Thus it not only decreases venous pressure but also increases blood flow.

Anatomic Arrangement: The conventional view of the muscle pump is based on the concept that the deep veins are compressed by contracting muscle and the superficial veins drain into the deep veins. The anatomic arrangement of the deep veins and their valves, set within and between the muscles of the limb, constitute a reciprocating pump mechanism. The arrangement is described as parallel reciprocating pumps (that empty reciprocally) that are linked in series extending along the length of the limb. The input from each pump comes from the deep vein below and from the superficial vein in the corresponding segment via the perforating veins. The blood is expelled towards the heart and competent valves are required to prevent retrograde flow from upstream veins.

In the lower leg, the deep veins are either intramuscular (the soleal sinuses and gastrocnemial veins) or intermuscular (the posterior and anterior tibial and peroneal veins). The soleal veins are large, thin walled, valveless sinuses, which act as pump chambers. The soleal sinusoids constitute the main collecting chambers of the calf muscle pump. The calf muscles are enclosed by a dense, inelastic covering (deep fascia). This tight fascial investment permits generation of high pressures within the muscle during contraction. This pressure is exerted on the muscle veins especially the soleal sinusoids and results in forceful expulsion of blood within them towards the heart.

Pathophysiology and calf pump failure: The normal functioning of the calf muscle pump depends on the integrity of the venous valves, patency of the deep veins, activity and strength of the muscles and mobility of the ankle and knee joints. Calf pump failure occurs as a result of the following:

Incompetent venous valves. The venous valves play an important role in calf pump function as they prevent retrograde flow of blood as the musculo-venous pumps propel blood from the lower leg towards the heart. Valve failure can occur in the superficial veins, which results in the development of varicose veins, or it can occur in the deep veins. Deep venous incompetence can occur as result of valve destruction following an episode of deep vein thrombosis or it can have a primary cause. As a result of this retrograde flow, especially in the deep veins, the calf pump is rendered ineffective and fails to effectively reduce venous pressures during exercise. This causes venous hypertension which can lead to skin changes and ulceration.

Obstruction of the deep veins: If the deep veins above the knee (Femoral, Popliteal, Iliac) are obstructed by thrombus following an episode of DVT, calf muscle pump function is affected as blood is ejected into vessels with reduced patency.

Muscle weakness/atrophy: The activity and strength of the muscle declines with ageing and as the strength of the muscle decreases so does the effectiveness of the calf pump.

Immobility of the ankle or knee joint: This also has an effect on calf pump function.

In summary, under normal conditions, blood in the veins of the lower leg is pumped by the action of the calf muscles, not by the heart. In a stationary, seated position, this normal physiological action is significantly reduced or absent.

DVT can strike any traveller, regardless of physical condition, age, or gender. A commonly held perception is that the condition is only related to long-haul journeys, this is not the case as DVT may present as a result of even short-term travel. Everyone who is inactive in a leg-cramped position for several hours is at risk. DVT is also not confined to those flying economy class. First-class passengers are also at risk, as are long distance auto and rail travellers. London's Heathrow Airport records one passenger death per month from DVT. One nearby hospital recorded thirty passenger deaths from DVT in a three-year period. DVT is the fourth leading cause of strokes in the United States. Approximately 2,000 Americans died from travel-related DVI-induced strokes in 2003.

Circumstances other than travel can also lead to DVT risks; for example, immobile patients in care homes, patients immobile during and post surgery, during prolonged bed rest, and patients with lower limb paralysis.

Risk factors for DVT have been identified which allow clinical stratification of patients into low, moderate and high-risk groups. Risk assessment depends on 'patient factors' and 'operation factors'. The 'patient factors' which signify a greater than average risk of DVI are: age >40 years, trauma, cancer, re-operation, infection, oestrogen therapy, obesity, renal transplantees, previous DVT or PE, established hypercoagulable states, neurological disorders, or varicose veins. In addition, surgery to the lower limb, particularly the hip and knee, gynaecological procedures, abdominal surgery and neurosurgery all carry a risk of DVT ranging from 14% in gynaecological surgery to approximately 50% in hip and knee replacement surgery. The methods available today for the prevention of DVT are pharmacological methods, which mainly reduce blood coagulability, and mechanical methods, which increase the rate of venous blood flow.

Mechanical methods of DVT prophylaxis include the use of graduated compression stockings; intermittent pneumatic compression, as well as foot impulse technology. Out of these methods, graduated compression stockings are the most widely accepted. Compression stockings have the advantage that they can be used during recumbency as well as during sitting, standing and walking.

Elastic compression stockings for DVT prophylaxis are graduated with pressures of 18 mmHg at the ankle, gradually reducing along the length of the leg (14 mmHg at the calf and 8 mmHg at the upper thigh). This pressure is sufficient to produce venous compression and an increased velocity of blood flow when the patient is supine, without affecting arterial inflow. The stockings are designed so that the tops do not become constriction bands around the thigh.

Elastic compression stockings have been shown to reduce venous dilatation as they reduce diameter and hence venous volume. They also cause an increase in venous flow velocity (blood flow velocity will increase as a result of narrowing of the venous diameter when the arterial inflow remains unchanged). Using Doppler ultrasound, it was shown that elastic stockings increase femoral vein blood flow velocity and the effect persists for up to 30 minutes after stocking removal. The increased venous flow velocity and decreased venous pooling, i.e. reduction of stasis may reduce the occurrence of venous thrombosis. However, stockings in the immobile patient do not facilitate muscle pump function in the lower limb.

Used alone, clinically appropriate use of stockings reduces the incidence of postoperative DVT by approximately 60% and when in combination with other preventative methods such as low dose heparin or intermittent pneumatic compression use of stockings may reduce the incidence by up to 85%. Stockings are also effective in reducing oedema.

Elastic compression is contraindicated in the presence of peripheral arterial disease. Stockings are often incorrectly fitted, or the wrong size and as a result the required compression gradients are not achieved. They can be uncomfortable to wear which causes poor patient compliance, they can also slip down the leg, and they are often difficult to apply (especially for the elderly). They can also cause superficial thrombophlebitis. Stockings must also be replaced every six months as frequent washing and wearing causes a loss of elasticity.

Intermittent pneumatic compression (IPC) has been commonly used in DVT prophylaxis. It can either be a single chamber device applying uniform compression to the whole limb, or it could exist as sequential chambers applying pressure in sequential fashion from the foot to the thigh (sequential compression device—SCD). Most commercially available SCD devices have a fixed cycle time of compression and deflation. More recently, new devices have been introduced which can detect changes in venous volume and respond by initiating the next compression cycle when the veins are considerably full. IPC can also be applied to the foot alone as a 'foot pump' (foot impulse technology). IPC is thought to work by increasing the rate of venous flow through the deep veins thus preventing stasis, which may lead to deep vein thrombosis. It has been shown to be more effective in DVT prophylaxis when used in combination with graduated compression stockings than on its own. IPC has been shown to enhance venous emptying of the limb and reduce oedema. It has also been suggested that external compression acts by encouraging the release of fibrinolytic activators from the venous endothelium and improve tissue fibrinolysis.

Arterial flow can be increased with intermittent compression. Intermittent pressure waves with pressure peaks at the systolic ankle pressure have been shown to increase blood flow in the large arteries and in the skin.

Limitations of intermittent pneumatic compression devices: These devices are often bulky and not portable and cannot be used when the patient is mobile. External pneumatic compression devices can also cause arterial ischemia. It must be also applied cautiously in patients with severe heart failure as it may result in a shift of the blood volume centrally.

There are a number of current strategies for prevention of travel-related DVT, which however are unsatisfactory for a number of reasons.

Exercise is primarily recommended, as activity of the lower limb, which will stimulate blood flow. Many airlines advocate an in-flight exercise programme, with particular attention to exercising the calf muscles. Observance of these programmes is generally poor and sporadic, thereby greatly reducing the value of this therapy. Additionally, there is no method for assessing passenger compliance, which may be of value from a legal standpoint. Furthermore, active movement throughout the cabin area is actively discouraged during turbulence and in general in response to the heightened terrorist threat.

Some practitioners suggest an Aspirin tablet before travelling, and at intervals during the trip, as an anti-coagulant. Most healthy people, however, are reluctant to take drugs as a purely speculative preventative measure. Furthermore, such an intervention should only be recommended by a medical healthcare professional who is familiar with the individual's medical history, as there are a number of significant risks associated with the use of aspirin. Again, there is no method for assessing compliance from a legal perspective.

Graduated compression stockings and socks have been provided by some airlines, or are available for purchase over the counter. These stockings are designed to exert a degree of compression at the ankle, with pressure gradually decreasing up the length of the hosiery. This action forces surface veins' blood into the deep vein system of the legs thereby supposedly correcting weak blood flow. Commercially available below knee graduated compression stockings tend to have a maximum compression at the ankle of 10-30 mmHg. This approach suffers from a number of problems, including the random nature of the applied pressure pattern each time the stocking is applied. Some commercial flight socks suggest they apply a pressure approximating 10 mmHg, which would appear to be of reduced value compared with the interface pressures advocated medically for surgical stockings.

Effective compression may not be achieved with a standardised sock shape, due to the highly variable shape of the lower limb. Moreover, the applied conditions are static, the foot, calf and thigh pumps inoperative, and therefore compression stockings may only offer limited reduction in DVT risk. The useful lifespan of such products is related directly to usage and care, with any proportional benefits decreasing rapidly with repeated usage. Finally, wearing of compression garments can be uncomfortable, and this alone may lead to reduced compliance.

A range of strategies exists for prevention of DVT in a clinical environment, which are unsatisfactory for a number of reasons.

For certain situations, in particular operating theatres, a variety of inflatable devices have been used to prevent DVT in the form of inflatable boots applied to each leg. As air is pumped into the boot, the leg is squeezed, forcing out the blood. These devices require pumps, and are rather obtrusive and cumbersome for use outside the operating theatre. Such systems are uncomfortable for the conscious patient and grossly inhibit any independent mobility when applied.

Devices and methods for electrical stimulation of leg muscles to reduce the risk of DVT are known. U.S. Pat. No. 5,674,262 describes a device which provides electrical stimulation of the calf muscle, together with a compression device used to compress the foot. U.S. Pat. No. 6,393,328 describes a multi functional electrical stimulation device which may be used to stimulate a variety of muscles, not only leg muscles. WO99/53996 describes a device which stimulates muscle twitch of the calf muscle, with the aim of reducing DVT. WO99/64105 describes a device for electrical stimulation of the calf muscle; the device incorporates a motion sensor for providing feedback to control the stimulation signal based on muscle contraction. DE 39 16 994 A1 describes a device having a longitudinal arrangement of several electrodes to provide stimulation along the length of the leg. WO03/063960 describes a device having electrodes integrated into a bandage housing which may be used to electrically stimulate the leg of a patient.

Prior art devices and methods have a number of shortcomings. One such shortcoming is that the devices must either stimulate muscles with a low level of contraction, which may not be sufficiently effective in promoting circulation to reduce DVT; or they may use higher levels of contraction, which will cause the muscles to contract sufficiently to cause movement of the limb, which may be undesirable in certain situations, and which may be painful.

It is among the intentions of the present invention to provide an alternative treatment for avoidance or reduction of the risk of DVT, SVI, and/or other circulatory disorders in the lower limb. This is achieved, in part, in certain embodiments of the invention by the use of electrical stimulation of lower limb muscles to obtain isometric muscle contraction in order to promote blood circulation. By isometric muscle contraction is meant contraction of opposing groups of muscles, such that protagonistic and antagonistic muscles or muscle groups are stimulated such that no or very little movement of the limb is effected.

The present invention may be additionally applied to the prevention, management and treatment of a range of disorders related to the dysfunctions of lower limb blood flow, including but not limited to ischaemia, ulceration, oedema, or phlebitis. Other disorders, including osteoporosis, heart failure, heart disease, common and pulmonary hypertension, may be treated.

SUMMARY OF THE INVENTION

According to a first aspect of the present invention, there is provided a method of enhancing blood circulation in a leg of a patient, the method comprising administering one or more electrical stimuli to a plurality of leg muscles sufficient to cause isometric contraction of the muscles. The leg muscles are preferably the calf muscle, although in certain embodiments of the invention, stimulation of the ankle and/or foot musculature may instead or in addition provide a suitable improvement in blood circulation. The leg muscles are preferably involved in a musculovenous pump; for example, the calf, foot, and/or thigh pumps.

The stimuli may be applied directly to the muscles, or indirectly via stimulation of a suitable nerve. For example, a favoured approach is to indirectly stimulate the lower limb musculature by accessing nerve groups in the area of the popliteal fossa. Unless otherwise specified, it will be appreciated that all reference herein to stimulation of a muscle is intended to encompass both direct stimulation and indirect stimulation.

These methods allow contraction of the calf or other leg muscles to take place even when the patient is otherwise immobile, and so allow the so called "calf pump" (or other musculovenous pump) to enhance and maintain effective blood flow.

A possibly undesirable effect of isolated contraction of the calf muscles is the plantar-flexion of the foot. In a seated individual (such as an airline passenger), this may cause the knee to rise, so making the process more obtrusive. Isometric contraction ensures that opposing muscles or groups of muscles are stimulated such that there is no or little movement of the limb as a result. The stimulus may be applied directly to posterior calf muscles; conveniently the soleus and/or gastrocnemius muscles. Indirect stimulation of the lower limb muscles may be achieved by electrical stimulation of the lateral popliteal nerve in the region of the popliteal fossa. Specifically at the inner margin of the biceps femoris muscle, behind the fibula at the inner side of the tendon of the biceps femoris. Additionally, indirect stimulation of the lower limb muscles may be further achieved by electrical stimulation of the medial popliteal nerve, which is located medially from the lateral popliteal nerve in the region of the popliteal fossa.

A second stimulus may be applied to shin muscles; conveniently the tibialis anterior. Preferably the second stimulus is applied simultaneously to the stimulus applied to the calf muscles. While this may not promote blood flow, application of a stimulus only to a posterior calf muscle may have the unwanted side effect of causing movement of the ankle joint. Application of a stimulus to the shin muscle will counteract any movement of the ankle joint caused by contraction of the calf muscle, so keeping the ankle and knee joints relatively still.

Alternatively, stimulation of the lateral popliteal nerve, in the region of the popliteal fossa, has the advantage of initiating the contraction of both posterior and anterior lower limb muscle groups. Such simultaneous stimulation results in isometric contraction; hence the ankle and knee joints would not be typically mobilised. Stimulation of the lateral popliteal also elicits contraction of the foot muscles and hence the so-called "Foot-pump" thereby further stimulating emptying of venous blood and enhancing blood flow. Additionally, the surprising advantage of selective stimulation of the lateral popliteal nerve is that the resultant muscular contractions are entirely compatible with standing and walking. An additional benefit of this mode of indirect stimulation is the involvement of the muscles in the sole of the foot, which have been shown to contribute substantially to clearance of blood from the lower leg.

In a clinical environment, where standing and walking are not a pre-requisite, the medial popliteal nerve may be stimulated, either in isolation or in combination with stimulation of the lateral popliteal nerve. A preferred version of dual medial and lateral popliteal nerve stimulation may result in near maximal contraction of the entire lower limb musculature, leading to enhanced efficiency and activity of both the calf and foot venous pumps, and by extension, movement of venous blood out of the lower limb, centrally towards the abdomen.

The method preferably comprises repeatedly administering an electrical stimulus to the muscles. Conveniently the stimulus is administered repeatedly for the duration of a journey or other temporary period of immobility.

A typical electrical stimulus may be at a current of between 0 to 100 mA, preferably 0 to 50 mA, more preferably 1 to 40 mA, and most preferably between 1 to 20 mA.

The stimulus may be an AC waveform, although it is preferably a DC waveform, more preferably a pulsed DC waveform. The stimulus may have a frequency of 0.01 to 100 Hz, preferably 0.1 to 80 Hz, more preferably 0.1 to 50 Hz; and most preferably 0.1 to 5 Hz. In other embodiments, the frequency may be from 30 to 60 Hz, and more preferably 40 to 50 Hz. Alternatively, a stimulus with a frequency from 0.1 to 1 Hz, or from 0.33 to 1 Hz may be used. The precise desired frequency may depend on the purpose of the method, and the general physical condition, age, sex, and weight of the patient, among other factors.

The stimulus may be applied for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient.

Characteristics of the stimulus may vary over time. For example, a single stimulus may increase in current over the duration of the stimulus. Preferably the increase is gradual up to a peak; the stimulus may then either be maintained at the peak; terminate at the peak; or decrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times.

Stimuli may be applied at a plurality of locations on the muscles. For example, stimuli may be applied along the main (long) axis of the leg. Such stimuli may be applied simultaneously, or preferably sequentially such that a 'wave' of stimuli proceeds along the leg. Preferably, such a wave proceeds upward toward the body of the patient. This wave effect serves to generate a corresponding wave of muscle contraction which wave may help to promote blood flow away from the leg.

The method may be utilised to initiate contractions of the musculature of the lower limbs in a sequence that is unrelated and asynchronous to the cardiac frequency. Alternatively, the stimulation may be timed in relation to cardiac activity. The application of the stimulation resulting in lower limb muscular contraction may be set at a predetermined variable interval after the QRS complex of the electrocardiogram, and the relaxation period either set at a predetermined variable interval after application of the stimulation signal or triggered by the QRS complex itself. The lower limb musculature may be timed to be at rest at the precise time that the heart pulse arrives at the leg, so that the pulse enters the leg without interference from the stimulating activity. The activation is reapplied at a subsequent time at which the pulse has substantially entered the leg, so that no interference with entry of the pulse into the leg results, and the effect of the stimulation combined with the pulse wave from the heart is to further promote movement of blood through the leg, improving the circulation.

The method may further comprise applying compression to the lower leg of a patient. The compression may be external and variable. For example, the stimuli may be administered in combination with use of a compression stocking or similar arrangement, in order to maintain pressure in the leg. Compression may be applied by means of a device which also carries electrodes or other means for administering electrical stimuli.

The method may further comprise the step of monitoring blood characteristics in the patient's lower leg. In particular, blood pressure and/or circulation may be monitored. Conveniently, the blood circulation may be monitored using photoplethysmography (that is, detecting reflected light from the skin, which is diagnostic of the blood content of peripheral vessels in the skin), or any other convenient means. The method may still further comprise the step of recording the monitored characteristics for later reference. For example, the monitored characteristics may be periodically written to a memory medium; after use the memory may be analysed to give an indication of the effectiveness of the method or to ensure that a patient used the method.

The method may further comprise the step of adjusting the stimulation in accordance with the monitored blood characteristic. For example, the degree of stimulation may be adjusted to a level sufficient to ensure a physiological level of blood circulation, but no greater. Alternatively, stimulation may be effected only at such times as the monitoring indicates that blood circulation has reduced below a certain level. This feedback method can help to maintain the stimulation at a minimum level to have some desired effects, while reducing the intrusiveness of the stimulation. It may be that use of the method will be encouraged when minimal stimulation is used.

According to a further aspect of the invention, there is provided a method of treatment of a condition characterised by impaired blood flow in lower limbs, the method comprising administering one or more electrical stimuli to a plurality of leg muscles sufficient to cause isometric contraction of the muscles. Preferably the calf muscle and/or the ankle and/or the foot musculature are stimulated. The condition to be prevented or treated may be include but is not limited to DVT, or management of ulcers, varicose veins, ischaemia, oedema, phlebitis, osteoporosis, peripheral vascular disease, coronary heart disease, heart failure, common and pulmonary hypertension.

According to a further aspect of the invention, there is provided a method of treatment of a condition characterised by impaired blood flow in lower limbs, the method comprising administering an electrical stimulus to the lateral popliteal and/ or medial popliteal nerves in the region of the popliteal fossa. These nerves innervate the lower limb musculature, with the resulting stimulation causing contraction of the anterior and posterior calf muscles and foot muscles. The condition to be treated may be selected from DVT prevention, or management of ulcers, varicose veins, ischaemia, oedema, phlebitis, osteoporosis, peripheral vascular disease coronary heart disease, heart failure, common and pulmonary hypertension.. A further aspect of the invention provides a method of operating a device for electrical stimulation of muscles, the method comprising the steps of attaching the device to leg muscles of a user to allow stimulation of said muscles; and electrically stimulating the muscles sufficient to cause the muscles to contract isometrically to elicit enhancement of venous blood flow. Preferably the muscle contraction does not cause any significant movement of the leg.

Also provided is a method of enhancing blood circulation in a leg of a patient, the method comprising monitoring cardiac activity of the patient; and administering an electrical stimulus to a leg muscle sufficient to cause the muscle to contract, wherein the stimulus is administered in time with a desired feature of the monitored cardiac activity. The cardiac activity may be monitored by obtaining an electrocardiogram of the patient, and stimulation resulting in lower limb muscular contraction may be set at a predetermined variable interval after the QRS complex of the electrocardiogram, and the relaxation period either set at a predetermined variable interval after application of the stimulation signal or triggered by the QRS complex itself. The lower limb musculature may be timed to be at rest at the precise time that the heart pulse arrives at the leg, so that the pulse enters the leg without interference from the stimulating activity. The activation is reapplied at a subsequent time at which the pulse has substantially entered the leg, so that no interference with entry of the pulse into the leg results, and the effect of the stimulation combined with the pulse wave from the heart is to further promote movement of blood through the leg, improving the circulation.

A further aspect of the invention provides a method of operating a device for electrical stimulation of specific nerve groups of the lower limbs, the method comprising the steps of attaching the device to the skin in the proximity of the lateral and/or medial popliteal nerves located in the region of the popliteal fossa of a user to allow stimulation of said nerves; and electrically stimulating the nerves innervating the musculature of the lower limb sufficient to cause sufficient contraction to elicit enhancement of venous blood flow.

According to a further aspect of the invention, there is provided a device for improving blood circulation in a lower limb of a patient, the device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically. The stimulus may be applied directly or indirectly to the muscle. The muscles may be calf muscles, or may be the ankle and/or foot musculature.

It is preferred that the applied electrical stimulus is efficacious in eliciting sufficient muscular contraction to promote movement of venous blood centrally towards the abdomen, and that the stimuli are painless and non-irritating to the user.

The control means is preferably a processor device having a stored program for activating the electrode.

The control means is preferably adapted to repeatedly activate the electrode.

The control means is preferably adapted to activate the electrode to deliver a current of between 0 to 100 mA, preferably 0 to 50 mA, more preferably 1 to 40 mA, and most preferably between 1 to 20 mA.

The control means may be adapted to activate the electrode to deliver an AC waveform, although preferably the control means is adapted to activate the electrode to deliver a DC waveform, more preferably a pulsed DC waveform. The waveform or pulse may have a frequency of 0.01 to 100 Hz, preferably 0.1 to 80 Hz, and most preferably 0.1 to 5 Hz. In other embodiments, the frequency may be 20 to 80 Hz, more preferably 30 to 60 Hz, and most preferably 40 to 50 Hz. Alternatively, a stimulus with a frequency from 0.1 to 1 Hz, or from 0.33 to 1 Hz may be used. The precise desired frequency may depend on the purpose of the method, and the general physical condition, age, sex, and weight of the patient, among other factors.

The control means preferably activates the electrode to deliver a stimulus for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient.

The control means may be adapted to vary characteristics of the stimulus over time. For example, a single stimulus may increase in current over the duration of the stimulus. Preferably the increase is gradual up to a peak; the stimulus may then either be maintained at the peak; terminate at the peak; or decrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times.

The device may comprise a plurality of electrodes for administering electrical stimuli to a leg muscle of a patient. The plurality of electrodes may be disposed linearly, such that in use the electrodes are disposed along the main (long) axis of a user's limb. The control means may be adapted to activate the electrodes to apply stimuli at a plurality of locations on the muscle. For example, stimuli may be applied along the main (long) axis of the leg. Such stimuli may be applied simultaneously, or preferably sequentially such that a 'wave' of stimuli proceeds along the leg. Preferably such a wave proceeds upward toward the body of the patient.

The device may comprise timing elements to integrate synchronous activation with components of the QRS complex of a measured electrocardiogram. The device may further comprise means for determining a QRS complex of a measured electrocardiogram; and may yet further comprise means for obtaining an electrocardiogram from a patient.

The device may comprise an array of electrodes. It is well established in conventional Functional Electrical Stimulation, when using direct nerve stimulation via superficial electrodes, that the current required to provide effective stimulation depends on the positioning of the electrodes. The closer the direct current path between electrodes passes to the nerve motor point in question, the less current is required. Similarly, a given current is more effective in eliciting a muscle contraction if it passes closer to the specific motor nerve point. This means that the effectiveness of a device comprising a simple pair of electrodes is highly dependent on the correct positioning of the electrodes. Advantageously, electrodes may be provided as an array, instead of a single pair. Arrays with complex geometries may be produced, for example using printed circuit techniques, by photo-etching, or by conductive ink printing, or by other techniques. The stimulator circuit can then address different pairs of electrodes in sequence, for example by means of a demultiplexer or analog switch. In one embodiment, the electrodes comprise 2 rows of electrodes. In sequence, each electrode is paired with its counterpart in the other row. Thus, the direct current path between electrodes moves incrementally as different pairs of electrodes are addressed. This effectively allows the device to scan across a region, so allowing the current path to pass very close to the optimum motor point when the optimum pair of electrodes is addressed. This makes the positioning of the device on the skin much less critical. The device may operate continuously in scanning mode for the duration of use. Thereby each time the limb is to be periodically stimulated, a sequence of pulses would be delivered to each electrode pair in turn. Alternatively, the device could be so arranged that an initial set-up after attaching the electrode included an identification of the optimum electrode pair. This could be achieved by user feedback, for example by pressing a button when the best contraction was achieved. Alternatively, the device may have the facility for measurement of blood clearance by PPG or other means; the device could identify the optimum electrode pair by this means. Having established the optimum electrode pair, it would then be possible to address specifically those electrodes during the periodic stimulation.

A further development of the above may comprise a 2-dimensional array of electrodes. A circuit could be produced by printed circuit technique, photoetching, conductive printing, or by other means, such that electrodes could be arranged into rows and columns 2-dimensionally. Thus, by addressing specific rows and columns by means of a demultiplexer or analog switch or other means, 2-dimensional electrode position can be selected. This provides the means for scanning as above, but in 2 dimensions to locate the optimum motor point. In one variation, the position of each electrode in the pair is addressable. In another variation, one electrode remains in a fixed position, but is paired with a 2-dimensionally selectable electrode, to allow positional control of the current path. For example, an 8×8 array, addressable by 16-bit demultiplexer or analog switch, provides for 64 selectable locations of current path.

In an alternative embodiment, a selectable array of positive electrodes may be arranged radially or spirally around a central negative electrode, or vice versa, to give segmentally scanning position of current path.

The device preferably comprises a second electrode for administering a stimulus to a shin muscle of a patient. A device with a single electrode may be possible, where the single electrode is sufficient to apply a stimulus to opposed muscles directly, or where the stimulus is applied to a single nerve location which stimulates opposed muscles. Preferably the control means is adapted to activate the second electrode simultaneously with the electrode for administering a stimulus to a calf muscle. Alternatively the leg muscle may be stimulated via the lateral popliteal nerve; advantageously contraction may be stimulated simultaneously to both anterior and posterior lower limb muscle groups.

The electrode(s) may be of a generally conventional type; for example, reusable type like some TENS applications or disposable electrodes of the type commonly used for ECG applications. The electrodes may be self-adhesive; repositionable; semi-adhesive; or may include a conductive gel for ensuring skin contact. Alternatively, the device may comprise a conductive gel, or may comprise an alternative conductive medium for interposing between the electrode and a user's skin. For example, the device may comprise a liner impregnated with a conductive gel or electrolyte for location between the electrode and a user. The liner may be conductive in restricted locations; for example, at a number of locations over the liner. This allows stimuli to be applied at a number of locations on a user's limb using only a single electrode.

The device may further comprise means for applying compression to the lower leg of a user. For example, the device may comprise a compression stocking or similar arrangement. The means for applying compression may also serve to carry one or more electrodes. For example, the electrodes may be mounted on a compression stocking, or on a band which fits around a user's leg, either in the calf area or on the knee area. Such a band may comprise neoprene or another similar elastic material. Alternatively, the electrodes may be mounted on an elastic material adapted to be wrapped around a user's leg; this allows the compression exerted by the material to be modified for different users.

In certain embodiments of the invention, the electrodes may be mounted on a band or wraparound material, which does not apply compression to the leg of a user. The use of a band or wraparound material allows placement of electrodes to be predetermined by their location on the band, such that a degree of variability in user's placing of the electrodes may be reduced.

The device may further comprise means for monitoring blood characteristics in the patient's lower leg. In particular, blood pressure and/or circulation may be monitored. Conveniently, the monitoring means may comprise a photoplethysmograph; conveniently this may comprise an LED and light sensor arranged such that the sensor detects light from the LED reflected from the user's leg.

The device may further comprise means for recording the monitored characteristics for later reference. For example, the recording means may comprise data storage means associated with the control means; the data storage means may be in the form of a solid state memory or similar.

The control means may further be adapted to adjust the activation of the electrode in response to the monitored blood characteristic. For example, the degree of stimulation may be adjusted to a level sufficient to ensure blood circulation, but no greater. Alternatively, stimulation may be effected only at such times as the monitoring indicates that blood circulation has reduced below a certain level.

The device may further comprise means for visually indicating when the electrode is activated; for example, an LED or other indicator may be activated when the electrode is. This provides a visual confirmation to a user that the device is functioning.

In certain embodiments, the control means of the device may be detachable from other components of the device. In particular, the control means may be detachable from the electrodes; in preferred embodiments, the electrodes are mounted on a support, and the control means is detachable from this support. The control means may be incorporated into a separate module; this module may also include a power supply, and other components where present, such as a visual indicator and/or blood pressure monitoring means. The module may include electrical contacts, which are engageable with corresponding contacts to connect the control means to the electrodes. The corresponding contacts may be located in a cradle or other receiving means, which receives the module comprising the control means. The cradle may also comprise mechanical engagement means, such as a detent or similar, to engage the module with the cradle. Alternatively, a magnetic engagement means may be used.

Also provided is a device for improving blood circulation in a lower limb of a patient, the device comprising at an array of electrodes for administering an electrical stimulus to leg muscles of a patient; a power supply connectable to the electrode array; and a control means for activating the electrode array to administer an electrical stimulus to the muscles sufficient to cause the muscles to contract.

A further aspect of the invention provides a device for improving blood circulation in a lower limb of a patient, the device comprising at least one electrode for administering an electrical stimulus to a leg muscle of a patient; and a module including a power supply and a control means for activating the electrode to administer an electrical stimulus to the muscle sufficient to cause the muscle to contract; the module being selectively engageable with the electrode. Preferably the muscle contraction is isometric.

A further aspect of the invention provides a device for improving blood circulation in a lower limb of a patient, the device comprising at least one electrode for administering an electrical stimulus to the skin in the proximity of the lateral and/or medial popliteal nerves located in the region of the popliteal fossa of a patient; and a module including a power supply and a control means for activating the electrode to administer an electrical stimulus to the nerves innervating the musculature of the lower limb sufficient to cause sufficient contraction to elicit enhancement of venous blood flow, the module being selectively engageable with the electrode. A still further aspect of the invention provides a module including a power supply and a control means for activating an electrode to administer an electrical stimulus to a leg muscle sufficient to cause the muscle to contract. The module may comprise a housing, and may further comprise electrical contacts for connecting the control means and power supply to external components.

A still further aspect of the invention provides a module including a power supply and a control means for activating an electrode to administer an electrical stimulus to the skin in the proximity of the lateral and/or medial popliteal nerves located in the region of the popliteal fossa. The module may comprise a housing, and may further comprise electrical contacts for connecting the control means and power supply to external components.

The present invention still further comprises a kit comprising a device comprising at least one electrode for administering at least one electrical stimuli to a plurality of leg muscles of a patient; a power supply connectable to the electrode; and a control means for activating the electrode to administer electrical stimuli to the muscles sufficient to cause the muscles to contract isometrically; together with instructions for the use of the device.

The present invention still further comprises a kit comprising a device comprising at least one electrode for administering an electrical stimulus to the skin in the proximity of the lateral and/or medial popliteal nerves located in the region of the popliteal fossa of a patient; a power supply connectable to the electrode; and a control means for activating the electrode to the nerves innervating the musculature of the lower limb sufficient to cause sufficient contraction to elicit enhancement of venous blood flow, together with instructions for the use of the device.

BRIEF DESCRIPTION OF THE DRAWINGS

The present invention will now be described by way of example only and with reference to the accompanying drawings, in which.

DETAILED DESCRIPTION OF THE DRAWINGS

Figure 1:
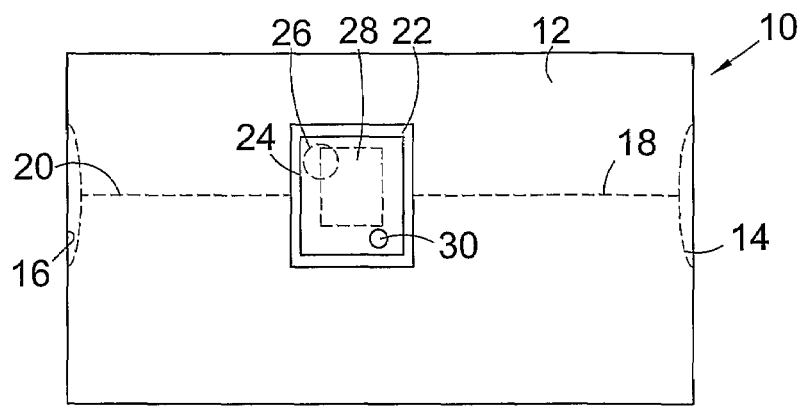
FIG. 1 shows an embodiment of a device for improving blood circulation in a lower limb of a patient in accordance with an embodiment of the present invention.

Referring first of all to FIG. 1, this shows an embodiment of a device for improving blood circulation in a lower limb of a patient. The device 10 includes a loop 12 of elasticated material which, in use, may be worn around a user's lower limb. On the interior surface of the elasticated material 12 are disposed first and second electrodes 14, 16 connected by conductive wires 18, 20 to a cradle 22 which is integral with the elasticated material 12.

Mounted within the cradle 22 is a control module 24, which includes a power cell 26, a control processor 28, and an external LED 30.

Figure 2:
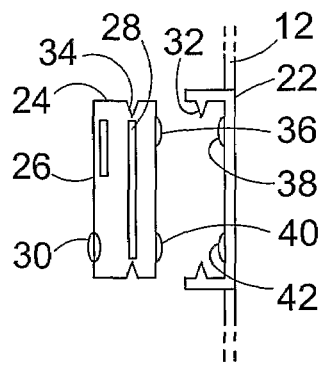
FIG. 2 shows the control unit and cradle of the device of FIG. 1.

The cradle 22 and control module 24 are shown in more detail in FIG. 2. The control module 24 is removable from the cradle 22, with a pair of detents 32 and corresponding recesses 34 allowing the cradle and control module to interlock. The control module and cradle carry corresponding electrical contact surfaces 36, 38, 40, 42 which provide for electrical communication between the control module 24 and the first and second electrodes 14, 16 via the conductive wires 18, 20.

Figure 4:
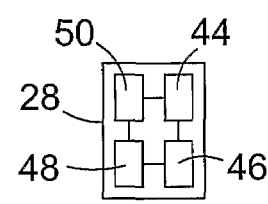
FIG. 4 is a schematic diagram of the control means of the present invention.

A schematic illustration of the control processor 28 is shown in FIG. 4. The processor 28 includes a timer module 44, a data store 46, a program store 48, and a logic unit 50.

In use, the device is operated as follows. The elasticated loop 12 is worn on a user's lower limb, such that the first electrode 14 is in contact with the calf muscle at the rear of the limb, and the second electrode 16 is in contact with the anterior muscle of the limb. When the control module 24 is engaged with the cradle 22, the device is automatically activated.

The program store 48 is preloaded with an operating program arranged to activate the electrodes each minute using a 40 Hz pulsed DC of 20 mA for 0.1 second. Both electrodes are activated simultaneously. The timer module 44 serves to generate appropriate timing signals, while the logic unit 50 executes the program of the program store 48.

As the electrodes 14, 16 are activated, the user's muscles are stimulated to contract. Contraction of the rear calf muscle, caused by the first electrode 14, serves to pump blood out of the leg using the calf pump thereby reducing pooling of the blood. Contraction of the anterior muscle, caused by the second electrode 16, is intended to reduce unwanted movement of the ankle by counterbalancing the contraction of the rear calf muscle. Simultaneously with each activation of the electrodes, the LED 30 on the outer surface of the control module 24 is also activated; this provides a visual confirmation that the device is operating.

The device is primarily intended for reduction of risk of DV, and may be worn for the duration of a flight or other long journey. When the journey ends, the user may detach the control module 24 from the cradle 22, thereby deactivating the device. The device may of course be used in situations other than journeys, for example, for bedridden or otherwise immobile patients, or during surgery or the like. The device may also be of benefit even to users who are not immobile, and may be used for example during exercise, physiotherapy or other activity to reduce the risk of blood pooling in the lower limbs. A number of other conditions may benefit from use of the device, including leg ulcers (arterial, venous, or diabetic), and varicose veins.

The control module 24 may be provided to the user in a sealed form, to be discarded when the power cell 26 is depleted. A replacement control module may then be fitted. In certain embodiments of the invention, a range of different control modules may be available, with a range of different pre-programmed patterns for activating the electrodes. A user may select a different module based on a number of different conditions (for example, user's physical health, length of journey, size of limb, and the like). Alternatively, the control module 24 may be partly user-programmable, to allow selection of one of a number of preset programmes from a single control module.

Figure 3:
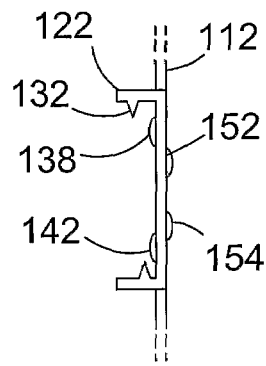
FIG. 3 shows an alternative cradle which may be used in a device of the present invention.

An alternative cradle 122 for use with a modified form of the device is shown in FIG. 3. This cradle 122 is intended to receive a similar control module to that shown in FIG. 2, and includes electrical contacts 138, 142, as well as detents 132. In addition to these components, the cradle 122 includes on its inner surface a further LED 152, and a photosensor 154. These act to allow plethysmography to be carried out on the user's leg. In use, the LED 152 and sensor 154 are located on the user's skin; periodically the LED 152 is activated by the control module to illuminate the user's skin; light is reflected from the skin and detected by the sensor 154. Using techniques known to those of skill in the art, the reflected light can be analysed by the logic unit 50 to yield information about the degree of blood flow within the peripheral circulation of the limb.

This information may then be recorded in the data store 46, to provide a record of the user's condition, and to confirm that the device was operated. Alternatively, or in addition, in certain embodiments of the invention the obtained information may be used to control the operation of the device. In particular, the device may be programmed to activate the electrodes not in a repeated cycle, but only when the sensed blood flow is below a certain level. In this way, the device will operate only when necessary to maintain blood flow, which may reduce the stimulation necessary for effective use. Similarly, the intensity of stimulation (e.g., current or duration) may be reduced when sensed blood flow is above a certain threshold.

Figure 5:
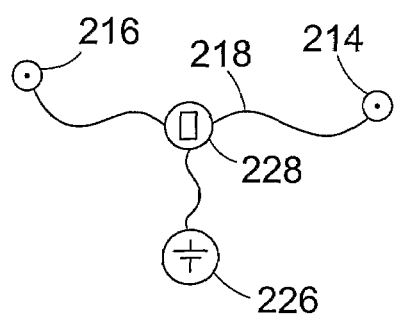
FIG. 5 shows an alternative embodiment of a device for improving blood circulation in a lower limb of a patient.

A further variation of the invention is shown in FIG. 5. Rather than using an elasticated loop, this embodiment of the invention uses separate housings containing a power cell 226, electrodes 214, 216, and control processor 228, each connected by conductive wires 218. Each of the housings may include an adhesive layer, which allows the housings to be secured to a user's skin, for convenience of use. Otherwise, the device operates in much the same way as that shown in FIG. 1.

Figure 6:
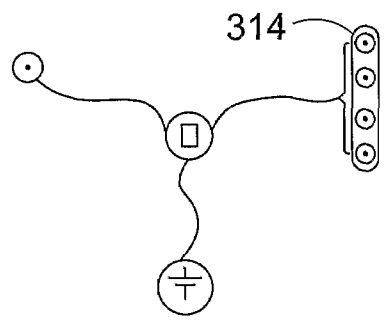
FIG. 6 shows a further alternative embodiment of a device for improving blood circulation in a lower limb of a patient.

A still further variation is illustrated in FIG. 6. This embodiment also includes separate housings, but has a modified first electrode housing 314, which comprises a number of separate electrodes on an adhesive strip. In use this strip is fastened to a user's leg, with the long axis of the housing running along the long axis of the leg. The electrodes are activated in sequence, from the lower end of the strip to the upper end of the strip. This arrangement may of course also be used with the device of FIG. 1.

The skilled person will understand that further variations on the invention described herein are possible. For example, rather than using a closed loop of elasticated material 12, a bandage of such material may be provided, which is looped around the leg by a user, so allowing a desired level of compression to be exerted. Alternatively, a loop may be arranged to be passed around a user's knee, with the electrodes extending downward from the loop, rather than being mounted within the loop.

Devices suitable for use in clinical settings, rather than those intended for personal use, may include more complex monitoring arrangements, or may include larger processors or power supplies. A separate power supply may also be used; for example, powered by mains electricity.

Other variations will be apparent to the skilled person.

Figure 7:
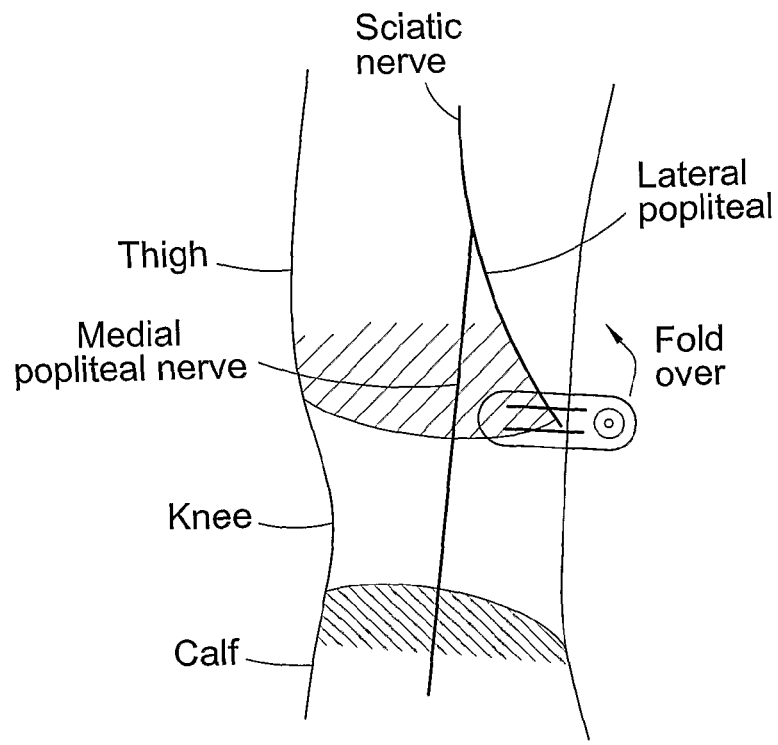
FIG. 7 illustrates the placement of a device on a patient's right leg so as to stimulate the lateral popliteal nerve.
Figure 8:
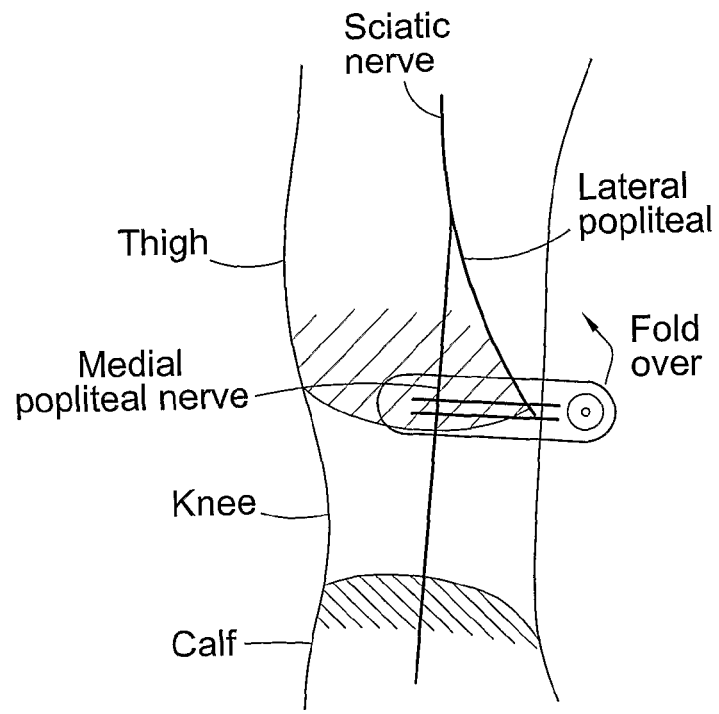
FIG. 8 illustrates the placement of a device on a patient's right leg so as to stimulate the lateral and medial popliteal nerve.
Figure 9:
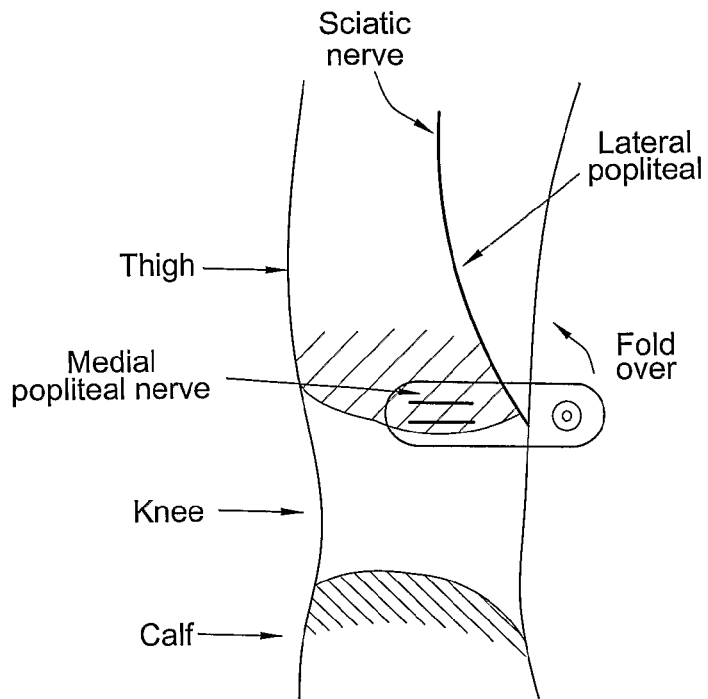
FIG. 9 illustrates the placement of a device on a patient's right leg so as to stimulate the medial popliteal nerve.
Figure 10:
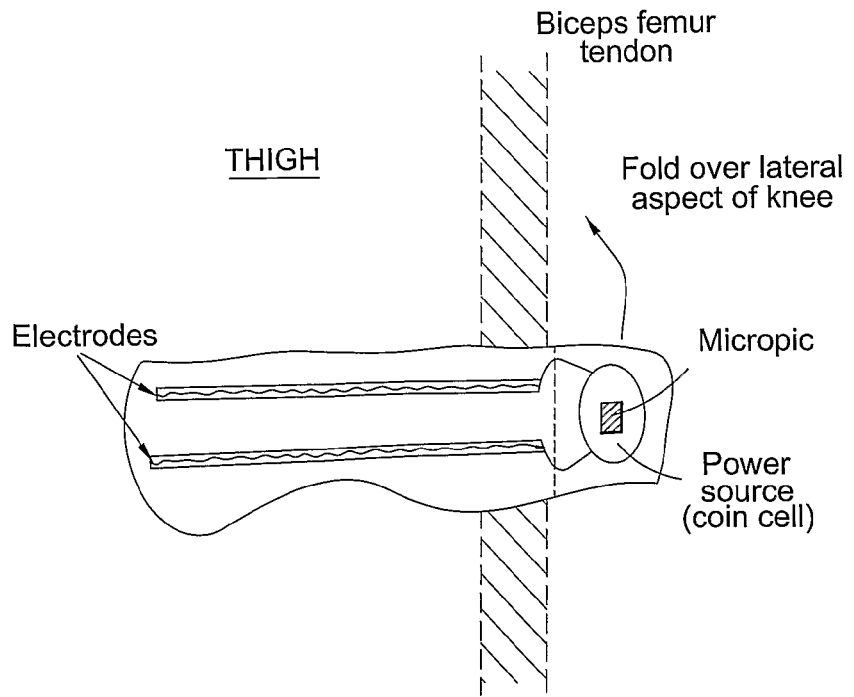
FIG. 10 is a posterior view of a patient's right knee showing a possible placement of electrodes.
Figure 11:
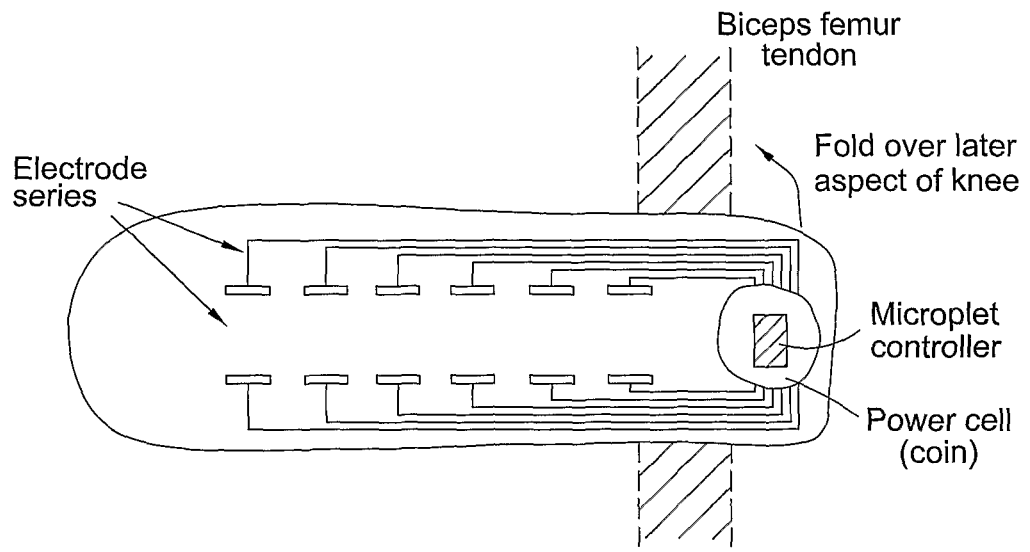
FIG. 11 is an alternative possible placement of an array of electrodes.

FIGS. 7 to 9 show possible placements of an electrode device on a user's leg (the illustrations show the right leg in posterior view) to stimulate respectively the lateral; the medial and lateral; and the medial popliteal nerve, FIGS. 10 and 11 show possible placements of an electrode device on a patient's knee (shown in posterior view of the right knee) having either two electrodes or two linear arrays of electrodes.

Figure 12:
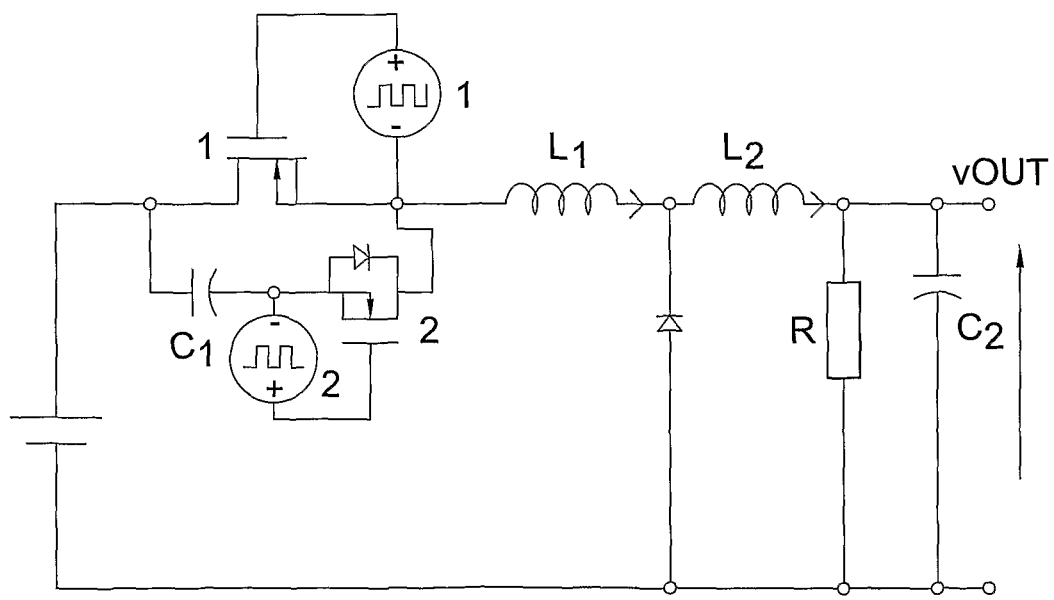
FIG. 12 shows a circuit suitable for use in controlling a device according to the present invention.

FIG. 12 shows a circuit which is suitable for controlling a device of the present invention, and particularly suitable for miniaturisation.

Figure 13:
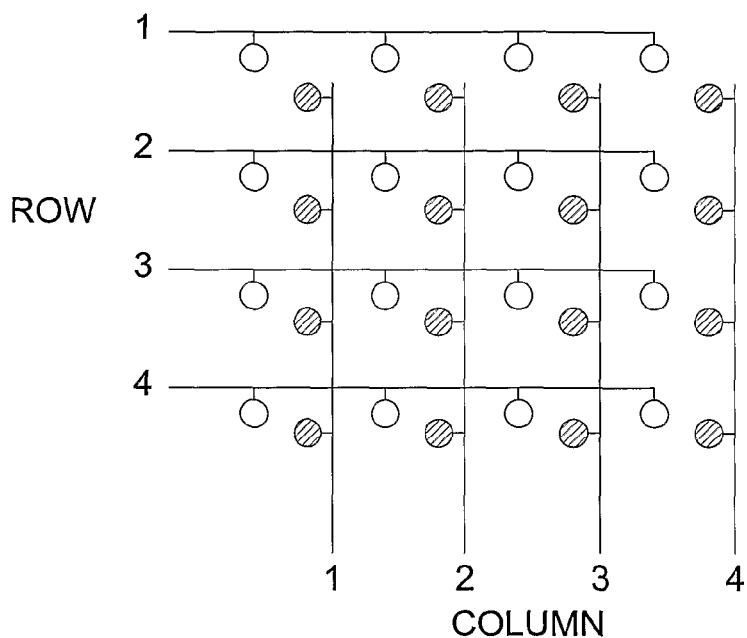
FIG. 13 shows a two dimensional array of electrodes for use with the present invention.

FIG. 13 shows a possible two dimensional electrode array which may be used with the present invention.

Figure 14:
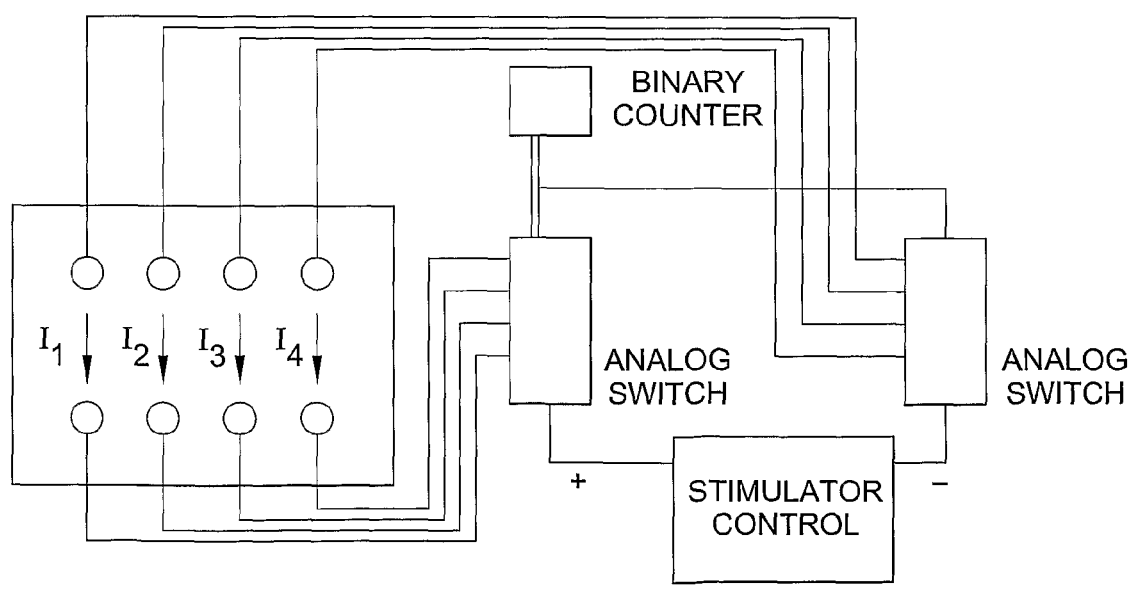
FIG. 14 shows a circuit suitable for controlling the array of FIG. 13.

FIG. 14 shows a circuit which may be used to drive the array of FIG. 13, to individually address specific electrodes.

Experimental Data
Blood Flow Measurement

All examinations were performed in a quiet, draught-free, temperature and humidity controlled laboratory (24° C.±1° C.; RH 30-40%). The subject had a light breakfast and avoided caffeine and fatty foods on the day of assessment and does not smoke. Lower limb blood flow was physiological normal with full competence of venous valves. Blood flow and muscular contraction was assessed while the lightly clad patient sat in a comfortable position with legs bent at the knee following a minimum equilibration period of ten minutes.

Photoplethysmography [PPG] is a non-invasive technique for the assessment of microcirculatory blood flow and is based upon changes in the intensity of transmitted light, which occurs due to the blood pulse in the tissue. Infra-red light (usually $\lambda \approx 850$ nm) from a source in a photoelectric PPG probe is used to illuminate the skin. The light undergoes multiple scattering, absorption, reflection and refraction in the illuminated skin and subcutaneous tissue. The emergent intensity of this light, measured by an adjacent photo-detector in the emitting probe, has been shown to be inversely proportional to the total blood flow in the illuminated tissue (Challoner A V J. (1979) Photoelectric plethysmography for estimating cutaneous blood flow. pp 125-51. In: Rolfe P, Ed. Non-invasive physiological measurements. New York: Academic Press.). The system used was a transducer/photopulse sensor model PH7A and photopulse adapter model PA13 (MedaSonics Ltd., California, USA). The system was set to the d/c recording mode and the transducer placed directly over a dorsal foot vein.

Strain-gauge plethysmography [SPG] is a non-invasive technique for the measurement of absolute peripheral blood volume. Transient circumferential changes of most parts of the body are related to their content of blood. Since the use of the mercury strain-gauge was first reported by Whitney in 1953 (Whitney R J. (1953) Measurement of volume changes in human limbs. J Physiol (London) 121:1-22), SPG measurements on the extremities have been acknowledged to be an objective method of assessing peripheral circulation. The system used were dual Hokanson EC-4 Plethysmographs (D. E. Hokanson, Inc. Washington, USA) together with gallium-Indium silastic strain-gauges (MedaSonics Ltd., California, USA). The circumference of the lower leg was measured at the distal and medial calf and appropriate gauges applied.

Functional Nerve Stimulation

Measurements of venous blood volume and muscular contraction were made during stimulation to the lateral popliteal nerve group in the posterior position.

Stimulation was effected by means of Faradic stimulation, using an inverter-type circuit. Faradic stimulation can be considered to be ac with pulse widths <1 ms (typically around 0.3 ms with a frequency <100 Hz (due to the absolute refractory period of normal muscle). In this instance single monophasic square pulses were used with a pulse width of 0.5 ms, to induce each individual contraction, Current required to produce the effects documented was 5-10 mA.

Data Acquisition

The data acquisition system allowed data for PPG, and SPG to be recorded simultaneously on a PC using a CED 1401-computer interface (Cambridge Electronic Design Ltd., Cambridge, UK.). This was used to record real-time analogue waveform signals sampling at 256 Hz from the monitoring equipment to generate a digital output.

Results

Figure 15:
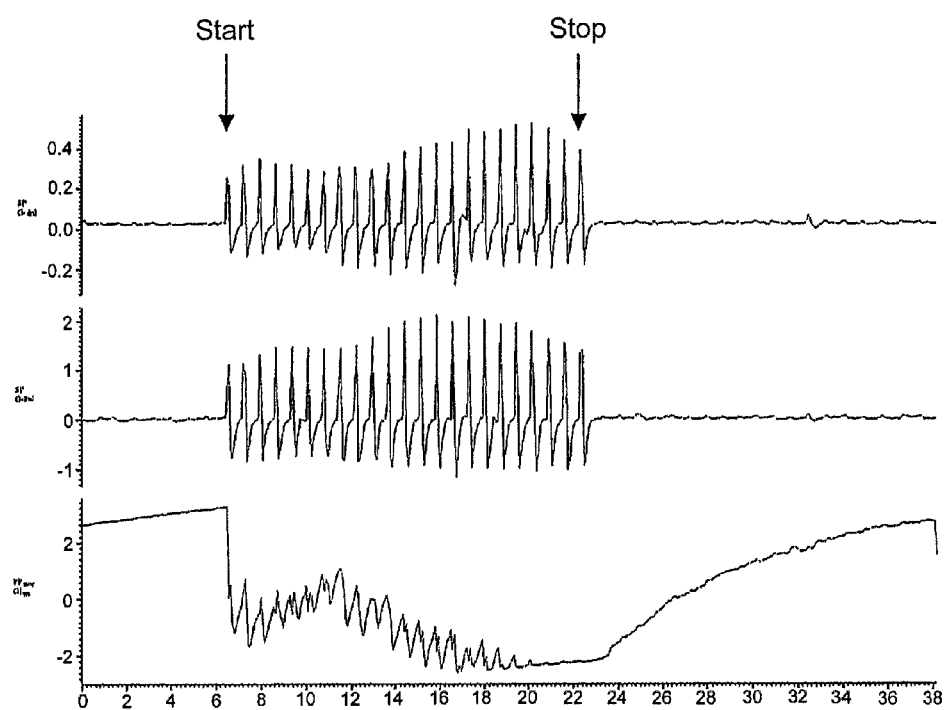
FIG. 15 shows experimental data from the use of a device on a patient.

The results are shown in FIG. 15. The graph shows three traces, reading from top of the figure downwards,

[1] Graph 1 is a strain gauge showing calf muscle contraction—distal position
[2] Graph 2 is a strain gauge showing calf muscle contraction—mid calf position
[3] Graph 3 is a PPG in d/c mode showing emptying of blood from the venous system in response to device activation and refilling of blood when the device is inactive.

The graph shows that the device encourages muscular contraction of the lower limb and emptying of blood from the venous system of the subject.

Comparison with Mechanical Compression Devices

We believe that the device and method described herein have equivalency of function to intermittent or segmental compression (pneumatic) devices. Specifically, controlled application of the described device and method to the lower limb will stimulate and activate a variety of physiological functions:

[a] Mechanical. When the musculature of the lower extremities is activated by the electro-stimulation device, blood is squeezed from the underlying deep veins and is accelerated in a proximal direction. This rapid movement of venous blood results in a sudden lowering of the venous pressure. Consequently, there is an increase in the difference between the arterial and venous pressures—the so-called AV gradient which then brings about a resultant increases in the arterial flow velocity.

[b] Biochemical. The increased blood velocity in both arterial and venous systems causes distension of the vessels in the lower limbs, resulting in increases in both compressive and shearing forces on the endothelial lining of the blood vessels. The mechanical forces resulting from increased blood volume and velocity stimulate release of endothelial factors such as nitric oxide, prostaglandins (e.g. prostacyclin) and activation of the fibrinolytic system, which exert potent vasodilator and anti-thrombotic actions. The physiological actions of these factors will have both local and systemic effects.

Furthermore, it is of particular note that intermittent or segmental compression (pneumatic) devices are generally contraindicated in peripheral vascular disease due to the compressive force they exert on the lower limbs, potentially further compromising peripheral blood flow. In contrast, the disclosed electro stimulation device in preferred embodiments exerts no such pressure on the lower limbs, but acts by stimulating the normal physiological processes found in walking.

Additional Applications of the Device and Method

Although the above description primarily refers to use of the method in connection with reduction or prevention of DVT, it will be apparent that various additional uses are possible. We describe here some of these further uses.

Treatment of Ulcers

Generally ischemic (arterial) ulcers appear on distal feet and toes, sites of diminished vascular perfusion. Ischemic symptoms include intermittent claudication and supine nocturnal pain, relieved by foot dangling. Compression therapy is usually contraindicated in the treatment of arterial ulcers because it exacerbates ischaemia.

A number of systemic conditions can lead to lower limb extremity ulcers. Leg ulcers comprise a diverse group of cutaneous diseases with different pathogenesis. The most common aetiology is vascular, such as peripheral arterial disease, venous disease, or circulatory pathology related to diabetes. It is estimated that 70 to 80% of lower leg ulcers fall within the category of "venous" disorders. Foot ulcers are both limb and life threatening for diabetics. After an initial amputation, the incidence of second amputation increases with a significant 5-year mortality. Other causes include: injuries—traumatic ulcers, dermatological, cardiovascular disease (stroke, angina, myocardial infarction), tumours, and infections such as the bacterium *Mycobacterium ulcerans*.

Chronic leg ulcers are a major health problem in the UK, affecting principally the elderly and costing up to £600 m per annum. The natural history of the disease is of a continuous cycle of healing and breakdown over decades. In Western countries, ten per thousand of the adult population are likely to have a chronic leg ulcer at some time. Studies report that about 60-80% of chronic leg ulcers have a venous component, 10-30% are associated with arterial insufficiency and that other factors include diabetes mellitus and rheumatoid disease. Arterial and venous insufficiency combined in 10-20% of cases.

The goal of venous ulcer therapy is to reverse the effects of venous hypertension. The combination of compression therapy and moist wound care will heal about 50% of venous ulcers. Compression choices include Unna's boot and its modifications: multilayer compression wraps, graduated compression elastic stockings, orthotic compression devices and pneumatic compression pumps.

Most of the clinical management of chronic leg ulcer falls to primary care: over 80% of chronic leg ulcers are cared for in the community, although a number will be found in hospital. Healing rates in the community are low. In specialised clinics the healing of smaller ulcers may be improved to 70% at three months in some circumstances. It is known that recurrence rates are certainly in excess of 67% and may be much higher. Available treatments can reduce recurrence rates to between 20% and 30%. There is clearly an ongoing requirement for novel, safe, and effective treatments.

Figure 16:
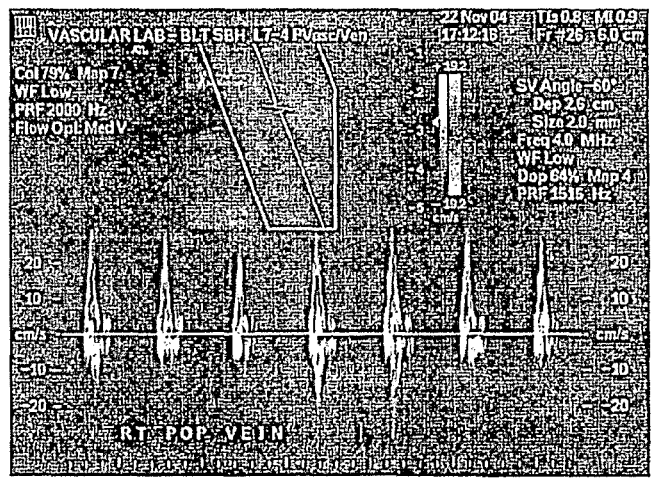
FIGS. 16 and 17 show additional experimental data from the use of a device on a patient.
Figure 17:
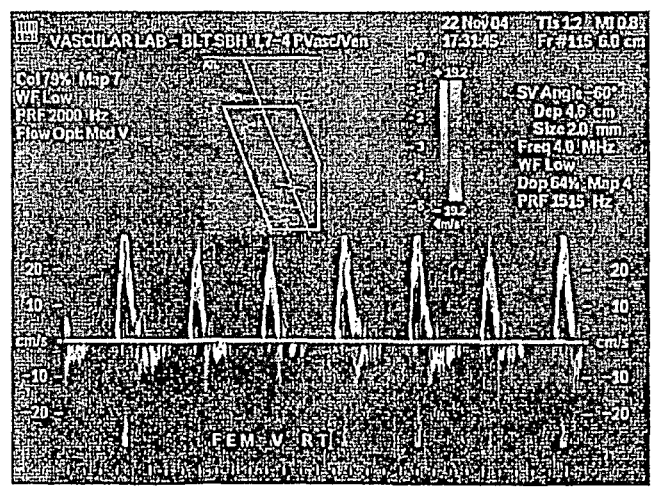

When the stimulator device is applied as described, the resultant muscular contractions of the lower limb are accompanied by emptying of blood from the venous vessels. This occurs in superficial venous vessels as exemplified by FIG. 15, and in larger order vessels such as the popliteal vein (FIG. 16) and femoral vein (FIG. 17). (conditions: FIG. 16: Stimulator settings 20 mA 1 Hz applied to the lateral popliteal nerve in the popliteal fossa with the subject sitting lightly clad, with the legs in a dependant position. ATL HDI 5000 Ultrasound, Linear array transducer 7-4 MHz. Peripheral Vascular Assessment, Venous Assessment. Right leg. FIG. 17: Stimulator settings 20 mA 1 Hz applied to the lateral popliteal nerve in the popliteal fossa with the subject sitting lightly clad, with the legs in a dependant position. ATL HDI 5000 Ultrasound, Linear array transducer 7-4 MHz. Peripheral Vascular Assessment, Venous Assessment. Right leg.)

Each stimulation by the device (to the lateral popliteal nerve) activates both the foot and calf pump vessels causing flow of blood centrally towards the heart. The emptying of blood from the lower limb venous system reduces lower limb venous pressure and reverses the effects of venous hypertension. Additionally, activity of the device will enhance lymphatic drainage and regulate excess tissue fluid concentrations.

Surprisingly, we have now demonstrated that there is an associated enhancement of the skin microcirculation as measured by Laser Doppler fluxmeter. Laser Doppler fluxmetry (LDF) is a technique, which uses laser light to measure the flux (velocity number) of blood cells, mainly erythrocytes, in the skin by the Doppler effect. A DRT-4 laser Doppler fluxmeter, (LDF; Moor instruments, Devon, UK) and 780 nm integrated probes were used in this study. Laser Doppler fluxmetry allows continuous, non-invasive, real time assessment of skin perfusion in hemispheric illuminated tissue under a measuring probe. The laser Doppler signal is generated by the movement of blood cells in both skin microvascular networks, i.e. the sub papillary thermoregulatory bed and nutritive capillaries, which more than 90% of it is generated by flow in sub-papillary vessels.

Figure 18:
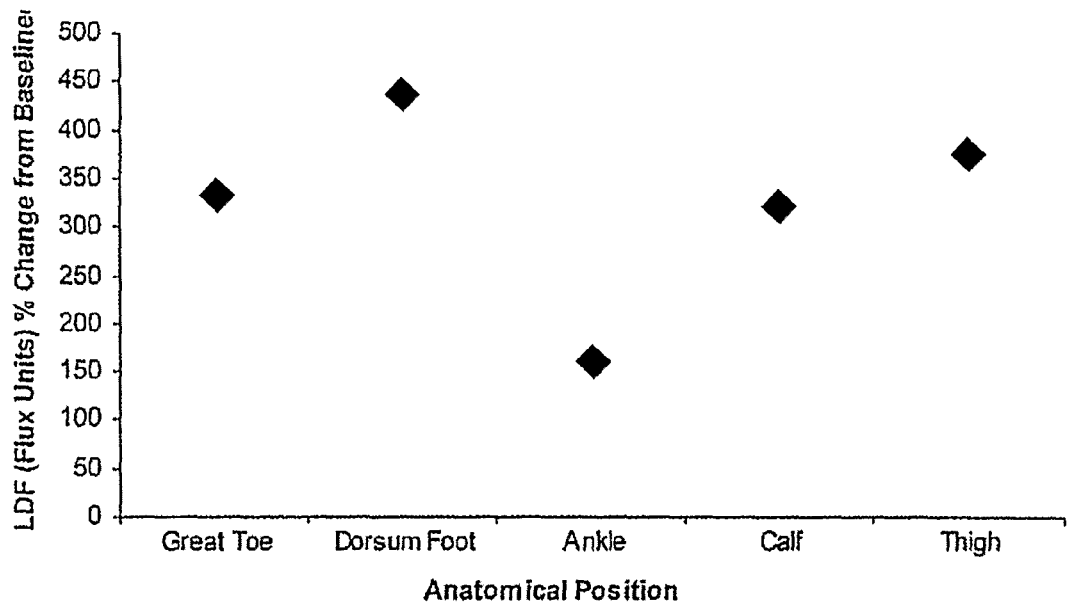
FIG. 18 shows change in flux of blood flow at various locations in the limb of a patient subjected to the method of the invention.

FIG. 18 illustrates that there is significant enhancement of microcirculatory (capillary) blood flow in response to controlled stimulation with the device. (Conditions for FIG. 18: Stimulator settings 20 mA 1 Hz applied to the lateral popliteal nerve in the popliteal fossa.)

The experiment took place in a temperature and humidity controlled room. Laser Doppler probes were applied to the skin of the left leg at various anatomical positions with the subject sitting, lightly clad, with the legs in a dependant position. Figure shows change from resting baseline due to stimulation by the device. A further aspect is that microcirculatory enhancement is also observed at the level of the thigh, which is proximal to the device and muscles undergoing contraction. The enhancements are observed when the device is active and return to normal resting levels when it is turned off. The alterations in microcirculatory blood flow in the lower limb are a result in part to reduced venous pressure downstream and part in response to the physical pumping action of the muscular contractions resulting from controlled stimulation with the device.

Figure 19:
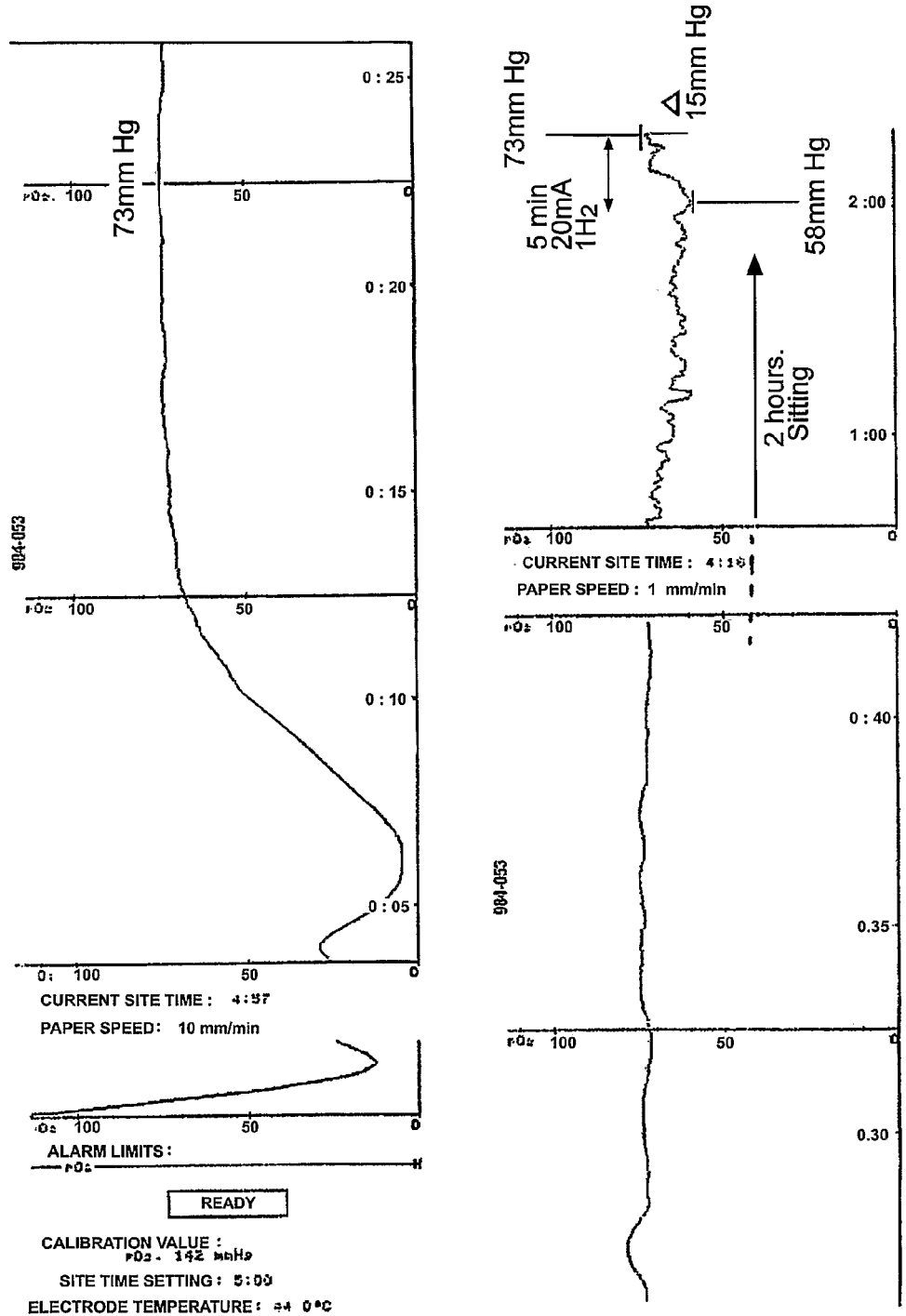
FIG. 19 shows oxygen levels in the blood of a patient subjected to the method of the invention.

Enhancement of microcirculatory blood flow in the skin of the lower limbs is associated with improved perfusion of blood, increased delivery of oxygen (FIG. 19) and nutrients to the tissues, increased removal of carbon dioxide and toxins from the tissues, and increased activity of the lower limb lymphatic system. All of which are generally associated with upregulation of local healing. (Conditions for FIG. 19: Stimulator settings 20 mA 1 Hz applied to the lateral popliteal nerve in the popliteal fossa. The experiment took place in a temperature and humidity controlled room. Transcutaneous oxygen (TCM3; Radiometer Copenhagen Ltd, Surrey, UK) was measured on the dorsum of the left foot during 2 hours with the subject sat, lightly clad, with dependent legs prior to stimulation. Follow equilibration of the device the resting TcPO2 level was 73 mmHg, falling to 58 mmHg after two hours. Complete recovery was rapidly achieved following stimulator activation (within 1-2 min)).

The beneficial physiological effects of the device leading to the physiological functions favouring healing of lower limb lesions (of all types and pathologies) mean that it is preferred that repeated and prolonged use is made of the described device and method in contrast to the intermittent and shorter duration application preferred for the prevention of thrombotic events associated with inactivity and travel.

Treatment of Dysfunctions of Systemic Circulation

The present method and apparatus may also be used for the management and treatment of the systemic circulatory effects of peripheral vascular disease (such as Intermittent claudication), Ischaemic heart disease (such as angina, myocardial infarction and heart failure), ischaemic organ disease (such as liver, kidney, intestine), cerebro-vascular disease, common and pulmonary hypertension. Aspects of the invention relate to methods of operating such a device, and to methods and apparatus for preventing, reducing or alleviating other pathologies and symptoms associated with dysfunction of the heart and systemic circulation.

It is estimated that 670,000 people in the UK suffer with heart failure and that this number will increase with the increasing incidence of cardiovascular disease. As well as the shortened life expectancy associated with this condition, significant morbidity leads to a poor quality of life in patients suffering heart failure.

One such significant feature of heart failure is peripheral oedema that is the result of fluid retention and impaired venous return. The major site of oedema is the lower leg, where not only does the swelling cause discomfort, but also leads to skin pathologies that result in ulceration and potentially infection.

Although diuretics reduce fluid retention in heart failure patients, poor venous return means that they remain susceptible to lower limb oedema. This can be improved by leg elevation or the use of graduated surgical stockings; however both these techniques have significant functional limitations and impact on the patients' quality of life.

Each stimulation by the device (to the lateral popliteal nerve) activates both the foot and calf pump vessels causing flow of blood centrally towards the heart. The emptying of blood from the lower limb venous system reduces lower limb venous pressure and increases the return of venous blood to the central cavity increasing perfusion to thoracic organs such as liver, heart and kidney. Enhancement of microcirculatory and venous blood flow of the lower limb is associated with improved perfusion of blood, increased delivery of oxygen and nutrients to the tissues, increased removal of carbon dioxide and toxins from the tissues, and increased activity of the lower limb lymphatic system. This approach represents the activity of the normal physiological mechanisms, which limit dependent oedema in healthy individuals. These mechanisms are inadequate in heart failure patients who have profoundly decreased mobility in addition to the other factors mentioned above. A reduction in lower limb oedema will significantly improve the quality of life of heart failure patients and improvements in outcome.

The beneficial physiological effects of the device leading to the physiological functions favouring reduction of lower limb oedema and improved cardiac function (of all types and pathologies) necessitate repeated and prolonged use of the described device in contrast to the intermittent and shorter duration application preferred for the prevention of thrombotic events associated with inactivity and travel.

Treatment of Osteoporosis

The present method and apparatus may also be used for the management and treatment of osteoporosis and other bone diseases. By facilitating microcirculatory blood flow within the bone, the device facilitates the building of new bone and/or prevents further local bone loss. Aspects of the invention relate to methods of operating such a device, and to methods and apparatus for preventing, reducing or alleviating other pathologies and symptoms associated with bone disease of the lower limbs.

The device may be used in conjunction with pharmaceutical interventions to enhance uptake of bone promoting compounds such as Vitamin D, bone morphogenetic proteins, bone remodelling inhibitors, and other drugs such as Zoledronate®.

It has been noted that people who become paralysed following spinal injury undergo dramatic losses in bone density during the year after injury. Bone density typically reduces by approximately 50% during this time. It has also been noted that astronauts lose significant bone density during protracted periods of zero gravity in space flight. These two facts have led to speculation as to the mechanism(s) of bone loss or bone maintenance in the skeleton. The suggestion is that mechanical loading of the bone is required for correct maintenance. For this reason, cyclic loading applied to the limbs by means of a vibrating plate has been adopted by some clinicians as a preventive therapy for bone loss following spinal injury. These therapies have as yet had inconclusive results.

Recently, alternative mechanistic theories have been proposed whereby bone loss may be attributed in part to decreased bone perfusion. Recently developed instrumentation has determined that perfusion of blood in the cortical bone is substantially reduced following spinal injury.

It has been established by the present inventors that contracting the muscles of the lower limb causes increased blood perfusion in the cortical bone. It is possible that lack of exercise or cyclic weight bearing on the bone has an effect on bone loss by means of its effect on blood perfusion. This would explain the doubtful efficacy of purely passive loading regimes such as those applied by vibration.

Studies using strain gauge instrumented skeletal components during ambulation have shown that forces experienced by the skeleton during ambulation are several times larger than those due to gravity alone. The reason for this is that to support the body during ambulation, the skeletal muscles must contract to apply reaction forces with unfavourable lever arms, and therefore with higher magnitudes than the net force applied to the ground. This means that passive loading in, for example, a standing frame, applies much smaller forces to the bones of the leg than those experienced during active loading by the muscles of the leg.

Activation of the leg muscles therefore achieves 2 effects that are desirable from the point of view of bone maintenance:

1) Application of substantial cyclic loading to the bone
2) Increased blood perfusion in the bone. in a seated position, forces may only be applied to the bones of the lower leg if those forces are opposed. This means that ideally, isometric contraction must occur in the posterior and anterior lower leg. The current invention describes a means of stimulation opposing muscle groups simultaneously, so achieving the desired effect.

Figure 20:
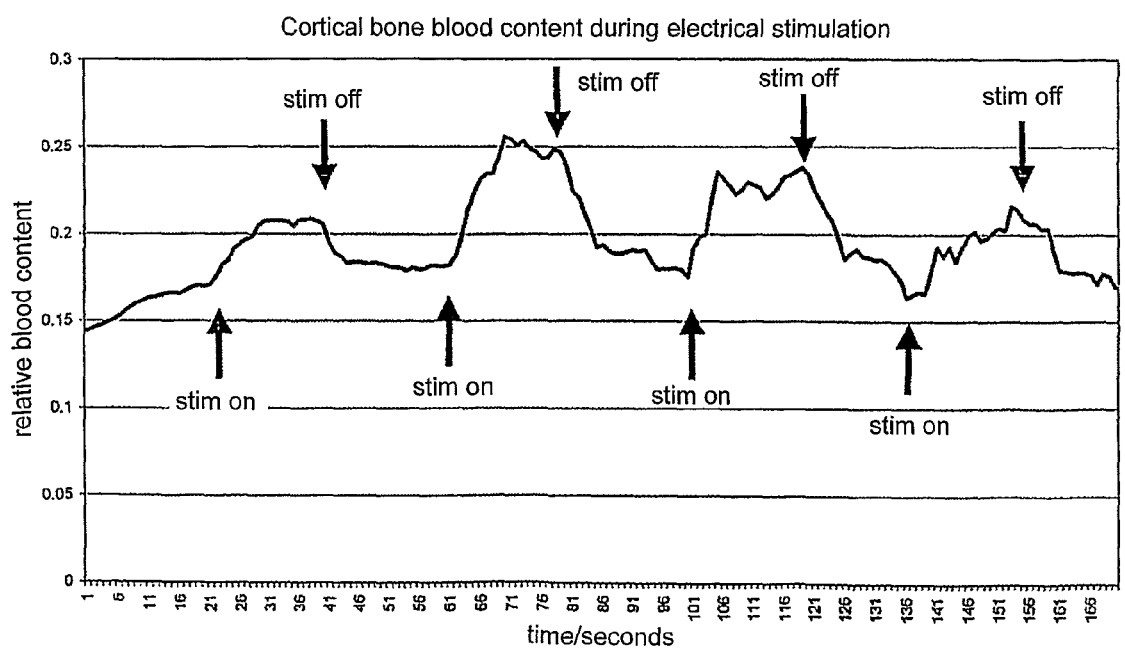
FIG. 20 shows cortical bone blood content in the limb of a patient subjected to the method of the invention.

FIG. 20 shows an experimental validation of the device: A healthy volunteer was fitted with the stimulator device to the right leg (Stimulator settings: 20 mA 1 Hz applied to the lateral popliteal nerve in the popliteal fossa). Cortical blood perfusion in the cortex of the tibia was measured continuously using near infrared spectroscopy. The experiment took place in a temperature and humidity controlled room. The subject sat, lightly clad with dependent leg prior to stimulation.

Initially, it can be seen that blood content rises slowly from baseline, owing to a pooling effect often observed in the vasculature of the lower leg resulting from gravitational effects. When the stimulation device is active, a significant increase in blood content is observed. Subsequent intermittent application of the muscle pump causes substantial fluctuations in blood content, indicating increased blood turnover, and therefore improved nutrient and/or pharmaceutical delivery and metabolite removal in the bone. The enhancements are observed when the device is active and return to resting levels when it is turned off.

This invention therefore additionally relates to a device for applying intermittent stimulation to the lower limb, which may be advantageously applied simultaneously to two opposing muscle groups, for the enhancement of blood supply to the bone. This has applications for the treatment or prevention of osteoporosis (and related pathologies) and healing in persons including but not limited to persons with spinal injuries, astronauts, elderly persons, persons confined to bed, and sedentary workers.

The beneficial physiological effects of the device leading to the physiological functions favouring reduction bone loss and enhanced bone maintenance necessitate repeated and prolonged use of the described device in contrast to the intermittent and shorter duration application preferred for the prevention of thrombotic events associated with inactivity and travel.

The invention claimed is:

1. A method of improving blood circulation in a leg of a patient, the method comprising:
   activating a plurality of leg muscles by administering one or more electrical stimuli to the lateral popliteal nerve in a region of the popliteal fossa, the electrical stimuli being sufficient to cause isometric contraction of the muscles.

2. The method of claim 1, wherein the isometric contraction stimulates opposing muscles or groups of muscles to result in little or no movement of the limb.

3. The method of claim 1, wherein the electrical stimuli is sufficient to cause isometric contraction of the calf muscles.

4. The method of claim 1, wherein the electrical stimuli is sufficient to cause isometric contraction of the muscles, in the absence of dorsiflexion mobilization of the ankle and knee joints as a consequence of the stimulation.

5. The method of claim 1, wherein administering one or more electrical stimuli comprises varying a characteristic of the stimuli over time.

6. The method of claim 5, wherein varying a characteristic of the stimuli over time comprises administering a single stimulus that increases in current over a duration of the stimulus.

7. The method of claim 5, wherein varying a characteristic of the stimuli over time comprises applying repeated stimuli, the characteristic of the stimuli varying between different stimuli.

8. The method of claim 1, further comprising monitoring blood characteristics in a lower leg portion of the patient.

9. The method of claim 8, wherein monitoring blood characteristics comprises recording monitored characteristics for later reference.

10. The method of claim 8, wherein monitoring blood characteristics comprises adjusting the stimuli in accordance with monitored blood characteristics.

11. The method of claim 1, wherein administering one or more electrical stimuli further comprises administering the stimuli to an ankle or foot muscle.

12. The method of claim 1, further comprising applying compression to a lower leg portion of the patient.

13. The method of claim 1, wherein administering one or more electrical stimuli comprises administering the stimuli repeatedly for a duration of a journey.

14. The method of claim 1, wherein administering one or more electrical stimuli comprises timing the stimuli in relation to cardiac activity.

15. A method of treatment of a condition characterised by impaired blood flow in lower limbs, the method comprising activating a plurality of leg muscles by administering one or more electrical stimuli to the lateral popliteal nerve in a region of the popliteal fossa, the electrical stimuli being sufficient to cause isometric contraction of the muscles.

16. The method of claim 15, wherein administering one or more electrical stimuli comprises treating or preventing the condition selected from the group comprising DVT, ulcers, varicose veins, ischaemia, oedema, phlebitis, osteoporosis, peripheral vascular disease, coronary heart disease, heart failure, common hypertension, and pulmonary hypertension.

17. A method of operating a device for electrical stimulation of muscles, the method comprising:
   attaching the device to a user in a region of the popliteal fossa to allow activation of said muscles by applying electrical stimulation to the lateral popliteal nerve in the region of the popliteal fossa; and
   activating the muscles by electrically stimulating the lateral popliteal nerve sufficiently to cause the muscles to contract isometrically.

18. A method of enhancing blood circulation in a leg of a patient, the method comprising:
   monitoring cardiac activity of the patient; and
   activating a plurality of leg muscles by administering an electrical stimulus to the lateral popliteal nerve in a region of the popliteal fossa, the electrical stimulus being sufficient to cause the muscles to contract isometrically, wherein the stimulus is administered in time with a desired feature of the monitored cardiac activity.

19. A device for improving blood circulation in a lower limb of a patient, the device comprising:
   a device body;
   at least one electrode for administration of an electrical stimulus to a nerve of a patient, the at least one electrode arranged with the device body so that the at least one electrode is positioned in the proximity of the lateral popliteal nerve in a region of the popliteal fossa;
   a power supply connectable to the electrode; and
   a control means of activating the electrode to activate a plurality of leg muscles by administering the electrical stimulus to the lateral popliteal nerve in the region of the popliteal fossa, the electrical stimulus being sufficient to cause the muscles to contract isometrically.

20. The device of claim 19, wherein the control means is adapted to repeatedly activate the electrode.

21. The device of claim 20, wherein the control means is adapted to vary characteristics of the stimulus over time.

22. The device of claim 19, further comprising a means for monitoring blood characteristics in the lower limb of the patient.

23. The device of claim 22 wherein the means for monitoring blood characteristics comprises a photoplethysmograph.

24. The device of claim 22, further comprising a means for recording the monitored characteristics for later reference.

25. The device of claim 22, wherein the control means is further adapted to adjust the activation of the electrode in response to the monitored blood characteristic.

26. The device of claim 19, further comprising a means for applying compression to a lower leg of a user.

27. The device of claim 26, wherein the means for applying compression carries one or more electrodes.

28. The device of claim 19, wherein the control means is detachable from other components of the device.

29. The device of claim 28, wherein the electrodes are mounted on a support, the control means being detachable from the support.

30. The device of claim 28, wherein the control means is incorporated into a separate module.

31. The device of claim 19, wherein the control means is a processor device having a stored program for activating the electrode.

32. The device of claim 19, further comprising a means for visually indicating when the electrode is activated.

33. The device of claim 19, further comprising timing elements to integrate synchronous activation with components of a QRS complex of a measured electrocardiogram.

* * * * *